(12) United States Patent
Noblitt et al.

(10) Patent No.: US 11,969,399 B2
(45) Date of Patent: *Apr. 30, 2024

(54) COMPOSITIONS AND METHODS FOR REMEDIATING CHEMICAL WARFARE AGENT EXPOSED SKIN

(71) Applicant: Armis Biopharma, Inc., Fort Collins, CO (US)

(72) Inventors: Scott Noblitt, Fort Collins, CO (US); Edwin D. Neas, Nunn, CO (US)

(73) Assignee: Armis Biopharma, Inc., Fort Collins, CO (US)

( * ) Notice: Subject to any disclaimer, the term of this patent is extended or adjusted under 35 U.S.C. 154(b) by 8 days.

This patent is subject to a terminal disclaimer.

(21) Appl. No.: 18/108,940

(22) Filed: Feb. 13, 2023

(65) Prior Publication Data

US 2023/0190688 A1 Jun. 22, 2023

Related U.S. Application Data

(60) Division of application No. 17/326,507, filed on May 21, 2021, which is a continuation-in-part of application No. PCT/US2021/012540, filed on Jan. 7, 2021, which is a continuation of application No. 16/900,816, filed on Jun. 12, 2020, said application No. PCT/US2021/012540 is a continuation of application No. 16/736,546, filed on Jan. 7, 2020, now abandoned, said application No. 16/900,816 is a continuation-in-part of application No. 16/736,546, filed on Jan. 7, 2020, now abandoned.

(60) Provisional application No. 63/004,858, filed on Apr. 3, 2020, provisional application No. 62/861,810, filed on Jun. 14, 2019, provisional application No. 62/530,045, filed on Jul. 7, 2017.

(51) Int. Cl.

| | |
|---|---|
| *A61K 31/19* | (2006.01) |
| *A61K 9/06* | (2006.01) |
| *A61K 31/327* | (2006.01) |
| *A61K 33/40* | (2006.01) |
| *A61P 17/02* | (2006.01) |
| *A61P 39/02* | (2006.01) |

(52) U.S. Cl.
CPC ............. *A61K 31/19* (2013.01); *A61K 9/06* (2013.01); *A61K 31/327* (2013.01); *A61K 33/40* (2013.01); *A61P 17/02* (2018.01); *A61P 39/02* (2018.01)

(58) Field of Classification Search
CPC .... A61K 31/19; A61K 31/327; A61K 9/0014; A61K 33/40; A61P 17/02

See application file for complete search history.

(56) References Cited

U.S. PATENT DOCUMENTS

| | | |
|---|---|---|
| 3,009,468 A | 11/1961 | Eberle |
| 3,365,487 A | 1/1968 | Gonse |
| 4,385,008 A | 5/1983 | Hignett |
| 4,403,994 A | 9/1983 | Hignett |
| 4,483,781 A | 11/1984 | Hartman |
| 5,055,287 A | 10/1991 | Kessler |
| 6,369,288 B1 | 4/2002 | Brown |
| 6,482,786 B1 | 11/2002 | Del Duca et al. |
| 6,491,896 B1 | 12/2002 | Rajaiah et al. |
| 6,492,443 B1 | 12/2002 | Kodemura et al. |
| 7,494,950 B2 | 2/2009 | Armitage et al. |
| 7,628,851 B2 | 12/2009 | Armitage et al. |
| 8,057,595 B2 | 11/2011 | Armitage et al. |
| 9,044,527 B2 | 6/2015 | Neas et al. |
| 9,283,202 B2 | 3/2016 | Neas et al. |
| 9,427,417 B2 | 8/2016 | Myntti |
| 9,844,219 B2 | 12/2017 | Neas et al. |
| 11,006,629 B2 | 5/2021 | Neas et al. |
| 2003/0235623 A1 | 12/2003 | Van Oosterom |
| 2004/0057868 A1 | 3/2004 | McVey et al. |
| 2005/0153857 A1 | 7/2005 | Sherry et al. |
| 2005/0197397 A1 | 9/2005 | Martin |
| 2005/0208094 A1 | 9/2005 | Armitage et al. |
| 2005/0229344 A1 | 10/2005 | Mittelstaedt et al. |
| 2007/0048175 A1* | 3/2007 | Tichy ............... A61K 8/19 422/28 |
| 2008/0226691 A1 | 9/2008 | Armitage et al. |
| 2009/0144925 A1 | 6/2009 | Orffeo |
| 2010/0016322 A1 | 1/2010 | Nagaraju et al. |
| 2010/0021558 A1 | 1/2010 | Dada et al. |
| 2010/0048763 A1 | 2/2010 | Armitage et al. |
| 2010/0108942 A1* | 5/2010 | Man ................ A01N 37/16 252/186.26 |
| 2012/0207806 A1 | 8/2012 | LoPesio |
| 2012/0213835 A1 | 8/2012 | Neas et al. |

(Continued)

FOREIGN PATENT DOCUMENTS

| | | | |
|---|---|---|---|
| CN | 103843817 A | 6/2014 | |
| DE | 202015001904 U1 * | 7/2015 | ............. A01N 31/02 |

(Continued)

OTHER PUBLICATIONS

DE-202015001904-U1 (Espacenet English translation, downloaded Apr. 2023) (Year: 2023).*

(Continued)

*Primary Examiner* — Mark V Stevens

(74) *Attorney, Agent, or Firm* — Fox Rothschild LLP

(57) ABSTRACT

The present invention relates to chemical and biological warfare agent decontaminating compositions and methods for using the same to decontaminate animal skin and wounds thereon exposed to the agents. The compositions may comprise a peracid, a hydroperoxide, and a peroxyacid.

9 Claims, 5 Drawing Sheets

(56) References Cited

U.S. PATENT DOCUMENTS

| | | |
|---|---|---|
| 2013/0018097 A1 | 1/2013 | Bolduc et al. |
| 2013/0251590 A1 | 9/2013 | Golden et al. |
| 2013/0330397 A1 | 12/2013 | Neas et al. |
| 2014/0113000 A1 | 4/2014 | Neas et al. |
| 2014/0120179 A1 | 5/2014 | Smith et al. |
| 2014/0249140 A1 | 9/2014 | Niquet et al. |
| 2014/0287154 A1 | 9/2014 | Kaiser et al. |
| 2015/0093425 A1 | 4/2015 | Moore |
| 2015/0133359 A1 | 5/2015 | Molnar et al. |
| 2015/0196526 A1 | 7/2015 | Neas et al. |
| 2016/0174553 A1 | 6/2016 | Matta et al. |
| 2017/0100335 A1 | 4/2017 | Hemmila et al. |
| 2017/0118991 A1 | 5/2017 | Neas et al. |
| 2017/0303538 A1 | 10/2017 | Neas et al. |
| 2020/0129383 A1 | 4/2020 | Neas et al. |
| 2020/0246511 A1 | 8/2020 | Noblitt |
| 2020/0276149 A1 | 9/2020 | Neas et al. |
| 2021/0077438 A1 | 3/2021 | Noblitt et al. |
| 2021/0337794 A1 | 11/2021 | Neas et al. |
| 2022/0023174 A1 | 1/2022 | Noblitt et al. |
| 2022/0030871 A1 | 2/2022 | Bui et al. |
| 2022/0226086 A1 | 7/2022 | Noblitt et al. |

FOREIGN PATENT DOCUMENTS

| | | | |
|---|---|---|---|
| EP | 0105689 A2 * | 4/1984 | ............. C07H 15/04 |
| EP | 1070505 A1 | 1/2001 | |
| EP | 2662330 A1 | 11/2013 | |
| EP | 2965624 A1 | 1/2016 | |
| EP | 1663333 B1 | 11/2018 | |
| GB | 1041983 A | 9/1966 | |
| GB | 2278057 A | 11/1994 | |
| JP | 60163902 A | 8/1985 | |
| JP | 5332679 B2 | 11/2013 | |
| WO | 200233038 A2 | 4/2002 | |
| WO | 2004020562 A1 | 3/2004 | |
| WO | 2010049892 A2 | 5/2010 | |
| WO | 2012128629 A1 | 9/2012 | |
| WO | 2014028633 A1 | 2/2014 | |
| WO | 2019010465 A1 | 1/2019 | |
| WO | 2019010467 A2 | 1/2019 | |
| WO | 2020069079 A1 | 4/2020 | |
| WO | 2020252402 A1 | 12/2020 | |
| WO | 2021142148 A1 | 7/2021 | |
| WO | 2021142152 A1 | 7/2021 | |

OTHER PUBLICATIONS

Alarcon et al., "Antimocrobial properties of magnesium chloride at low pH in the presence of anionic bases", Magnes Res (2014), 27:57-68 (Abstract only).

Davies et al., "A convenient preparation of aqueous methyl hydroperoxide and a comparison of its reactivity towards triacetylethylenediamine with that of other nucleophiles: the mechanism of peroxide bleach activation", Journal of Chemical Society, Perkin Transactions 2, 1992, pp. 559-562.

Extended European Search Report dated Mar. 16, 2021 in Application No. 18828616.5 (8 pages).

Osovsky et al., "Decontamination of Adsorbed Chemical Warfare Agents on Activated Carbon Using Hydrogen Peroxide Solutions", Environmental Sci and Tech (2014), 48:10912-10918.

International Search Report and Written Opinion dated Mar. 26, 2021, in Application No. PCT/US2021/012536 (8 pages).

International Search Report and Written Opinion dated Mar. 26, 2021, in Application No. PCT/US2021/012540 (8 pages).

International Search Report and Written Opinion dated Sep. 24, 2018, in Application No. PCT/US2018/041163 (9 pages).

International Search Report and Written Opinion dated Sep. 9, 2020, in Application No. PCT/US2020/037616 (14 pages).

Jacks et al., "Evaluation of Peracid Formation as the Basis for Resistance to Infection in Plants Transformed with Haloperoxidase", Journal of Agricultural and Food Chemistry, 2002, 50: 706-709 (see abstract).

Madronich, S., "Chemical Evolution of Gaseous Air Pollutants Down-Wind of Tropical Megacities: Mexico City Case Study" Atmospheric Environment, 2006, vol. 40, pp. 6012-6018.

* cited by examiner

FIG. 1

| Decon | N | 24 hr Probit Estimates | | | Est. PR[1] |
|---|---|---|---|---|---|
| | | LD50 µg/kg, p.c. | Delta 95% CI | Slope | |
| Water | 25 | 3198 | 2760 - 3706 | 12.1 | 23 |
| 1% Dawn™ Det. | 29 | 3622 | 2926 - 4484 | 7.4 | 26 |
| RSDL-G[2] | 37 | 5287 | 4792 - 5832 | 11.4 | 38 |
| RSDL-S[3] | 25 | 6912 | 5920 - 8070 | 11.0 | 49 |
| 2% Composition | 41 | 15160 | 14209 - 16174 | 20.8 | 108 |

1. Estimated using 140 µg/kg in denominator of the Protective Ratio (PR)
2. Applied with gauze
3. Applied with commercial sponge pad

COMPOSITIONS AND METHODS FOR REMEDIATING CHEMICAL WARFARE AGENT EXPOSED SKIN

CROSS-REFERENCE TO RELATED APPLICATION

This application is a divisional application of U.S. patent application Ser. No. 17/326,507 filed May 21, 2021, which claims priority benefit under 35 U.S.C. § 120 as a Continuation In Part of International Patent Application No. PCT/US21/12540 filed Jan. 7, 2021, which in turn claims priority under 35 U.S.C. § 120 to U.S. patent application Ser. No. 16/900,816, filed Jun. 12, 2020, and U.S. patent application Ser. No. 16/736,546, filed Jan. 7, 2020. U.S. patent application Ser. No. 16/900,816 is a Continuation in Part of U.S. patent application Ser. No. 16/736,546, which is a Continuation In Part of International Patent Application No. PCT/US2018/041163, filed Jul. 7, 2018, which claims priority under 35 U.S.C. § 119(e) to U.S. Provisional Application No. 62/530,045 filed Jul. 7, 2017. U.S. patent application Ser. No. 16/900,816 also claims priority under 35 U.S.C. § 119(e) to U.S. Provisional Application No. 62/861,810, filed Jun. 14, 2019 and U.S. Provisional Application No. 63/004,858, filed Apr. 3, 2020. The disclosures of each of the foregoing applications are incorporated by reference herein in their entirety.

FIELD OF THE INVENTION

The present invention relates to compositions that are useful for surface decontamination after chemical or biological warfare agent exposure and methods for producing and using the same. The compositions may contain a peroxyacid the corresponding carboxylic acid, and a hydroperoxide.

BACKGROUND OF THE INVENTION

The skin is a primary route of exposure to chemical agents used as weapons of mass destruction. Because of this threat, the U.S. military has invested considerable resources in developing detectors, protective garments, and products to remove and/or decontaminate chemical agent exposure to the skin. The currently fielded skin decontamination (DC) product is a lotion known as Reactive Skin Decontamination Lotion (RSDL), which is a mixture of potassium 2,3-butanedione monoximate (KBDO) and diacetylmonoxime (DAM) in a solvent of polyethylene glycol monomethyl ether (MPEG) and water. RSDL is FDA approved for use on the skin, near eyes, around wounds and equipment against all OP chemical agents, sulfur mustard and T-2 toxin.1 Military personnel are issued three pouches of RSDL; each pouch contains three packets with a sponge pad saturated with RSDL. After a suspected exposure to a chemical agent, RSDL is applied by scrubbing the exposed area(s) vigorously with the sponge and allowing it to remain on the skin for at least 2 minutes before removing. 2,3 RSDL can be reapplied and left on the skin for up to twenty-four hours. While RSDL is an effective broad spectrum DC product, the user community has complained about its expense and some of the physical characteristics of the product. This has renewed interest in identifying a more acceptable broad spectrum personal DC product.

SUMMARY OF THE INVENTION

One aspect of this invention provides an aqueous decontaminating composition containing one or more peroxyacids in an amount ranging from about 0.0001% to about 20% by weight; one or more hydroperoxides in an amount ranging from about 0.01% to about 25% by weight; and one or more carboxylic acids in an amount ranging from about 0.01% to about 30% by weight, wherein at least one of the carboxylic acids is the parent carboxylic acid of the peroxyacid. In one embodiment, at least one of the hydroperoxides is hydrogen peroxide. In another embodiment, the amount of the hydroperoxide ranges from about 5% to about 25% by weight. In a further embodiment, the one or more carboxylic acids are selected from C2-10 carboxylic acids, dicarboxylic acids, tricarboxylic acids, β-keto carboxylic acids, and mixtures thereof. In yet a further embodiment, the amount of the carboxylic acid ranges from about 5% to about 22% by weight In one embodiment, the peroxyacid is peracetic acid. In another embodiment, the peroxyacid is peracetic acid and the parent carboxylic acid is acetic acid. In a further embodiment, the amount of the peroxyacid ranges from about 0.02% to about 6% by weight. In one embodiment, the composition further contains a stabilizer selected from the group consisting of etidronic acid, disodium ethylenediaminetetraacetic acid, ethylenediaminetetraacetic acid, tetrasodium ethylenediaminetetraacetate, citramalic acid, dipicolinic acid, dipicolinic acid N-oxide or a combination thereof. In another embodiment, the composition further containing a magnesium salt. In a different embodiment, the magnesium salt is the magnesium salt of peracetic acid. In a further embodiment, the magnesium salt is magnesium acetate tetrahydrate.

In another embodiment, the composition is an aqueous solution containing: peracetic acid in an amount ranging from less than 1% to about 10% by weight; hydrogen peroxide in an amount ranging from about 5% to about 20% by weight; and acetic acid in an amount ranging from about 5% to about 20% by weight.

In another embodiment the decontaminating composition is an aqueous composition containing: peracetic acid in an amount ranging from about 0.0001% to about 3.5% by weight; hydrogen peroxide in an amount ranging from about 0.01% to about 12% by weight; and acetic acid in an amount ranging from about 0.01% to about 12% by weight. In one embodiment, the composition is capable of decontaminating at least one of human skin, human wounds, or non-human surfaces that have been exposed to a chemical biological warfare agent. In another embodiment, the composition is capable of decontaminating at least one of V-series nerve agents, G-series nerve agents, A-series nerve agents, and mustard agents.

A different aspect of the invention provides a method of decontaminating skin, wounds, or surfaces, comprising contacting human skin, a human wound or a non-human surface that has been exposed to a chemical or biological warfare agent, with an amount of the decontaminating composition that is sufficient to decontaminate the skin, wound or surface. In another embodiment, the chemical warfare agent is selected from a V-series nerve agent, G-series nerve agent, A-series nerve agent, mustard agent, or a combination thereof. In a further embodiment, the composition is formulated in a form selected from the group consisting of a gel, sol, liquid, lotion, irrigation gel, spray, or a combination thereof. In yet a further embodiment, the decontamination composition is contacted with the human skin, human wound or non-human surface by at least one of: soaking the human skin, human wound or nonhuman surface in a solution of the composition, dispensing a pressurized solution of the composition onto the human skin or the surface, or applying a coating or layer of the composition on the human skin, human wound or nonhuman surface.

BRIEF DESCRIPTION OF THE FIGURES

The accompanying drawings, which are incorporated herein and constitute part of this specification, illustrate the presently preferred embodiments of the invention, and, together with the general description above and the detailed description given below, serve to explain the features of the invention. In the drawings:

Figure 1:
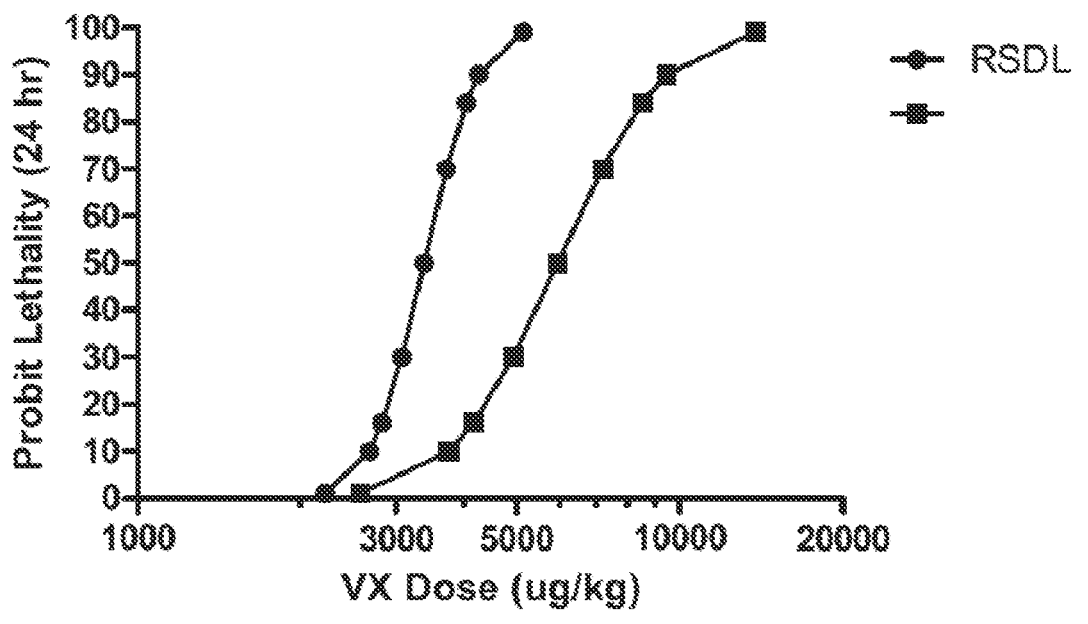

FIG. 1 is a graph of the VX dose lethality curves in animals decontaminated with either RSDL or a composition according to the invention after cutaneous exposure.

DETAILED DESCRIPTION OF THE INVENTION

Figure 2:
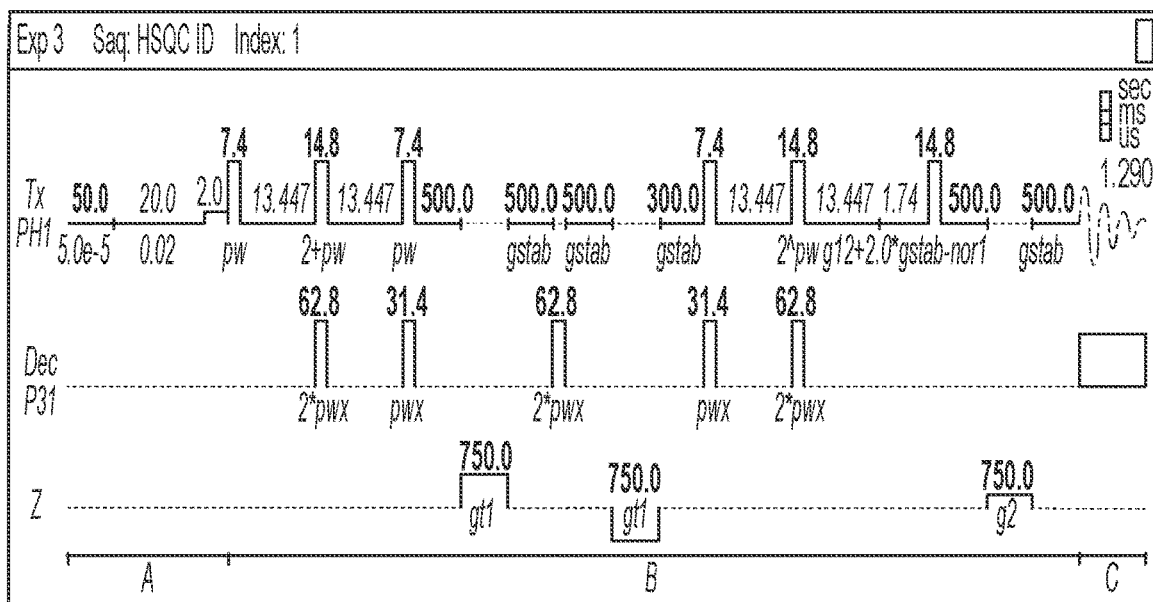
FIG. 2 is a depiction of a pulse sequence of modified gradient $^1$H-X 1D-HSQC for chemical warfare agents (CWAs).

While various aspects and features of certain embodiments have been summarized above, the following detailed description illustrates a few embodiments in further detail to enable one of skill in the art to practice such embodiments. The described examples are provided for illustrative purposes and are not intended to limit the scope of the invention.

In the following description, for the purposes of explanation, numerous specific details are set forth in order to provide a thorough understanding of the described embodiments. It will be apparent to one skilled in the art, however, that other embodiments of the present invention may be practiced without some of these specific details. Several embodiments are described herein, and while various features are ascribed to different embodiments, it should be appreciated that the features described with respect to one embodiment may be incorporated with other embodiments as well. By the same token, however, no single feature or features of any described embodiment should be considered essential to every embodiment of the invention, as other embodiments of the invention may omit such features.

The invention relates to compositions that are useful for decontamination of surfaces exposed to chemical or biological warfare agents. The invention also relates to methods of producing and using the compositions. The compositions overcome the problems of the prior art by providing an aqueous composition containing a peroxyacid, the corresponding carboxylic acid and a hydroperoxide.

The terms "peroxyacid," "peracid," "percarboxylic," and "peroxy-carboxylic acid," are used interchangeably herein. In general, peroxyacids are compounds of oxidized form of a base organic acid (generally a carboxylic acid) that exist in equilibrium with an oxidizer (generally hydrogen peroxide) and water. Peroxyacids have the formula $R(CO_3H)_n$, where, for example, R is an alkyl, arylalkyl, cycloalkyl, aromatic, or heterocyclic group, and n is one, two, or three, and named by prefixing the parent acid with "peroxy-." The R group can be saturated or unsaturated as well as substituted or unsubstituted. Peroxycarboxylic acids can be made by the direct action of an oxidizing agent on a carboxylic acid, by autoxidation of aldehydes, or from acid chlorides, and hydrides, or carboxylic anhydrides with hydrogen or sodium peroxide.

Peroxyacids useful in the compositions and methods of the present invention include peroxyformic, peroxyacetic, peroxypropionic, peroxybutanoic, peroxypentanoic, peroxyhexanoic, peroxyheptanoic, peroxyoctanoic, peroxynonanoic, peroxydecanoic, peroxyundecanoic, peroxydodecanoic, or the peroxyacids of their branched chain isomers, peroxylactic, peroxy-maleic, peroxyascorbic, peroxyhydroxyacetic, peroxyoxalic, peroxymalonic, peroxysuccinic, peroxyglutaric, peroxyadipic, peroxypimelic and peroxy-suberic acid and mixtures thereof.

In some embodiments, the peroxyacid is either a C1 to C11 peroxycarboxylic acid, C2 to C6 peroxycarboxylic acid, C1 to C4 peroxycarboxylic acid, or a C5 to C11 peroxycarboxylic acid. In some embodiments, the compositions of the invention utilize a combination of several different peroxycarboxylic acids. For example, in some embodiments, the composition includes one or more C1 to C4 peroxycarboxylic acids and one or more C5 to C11 peroxycarboxylic acids. In one embodiment, the peroxyacid is peracetic acid (C2), peroxy propionic acid (C3), peroxybutanoic acid (C4), peroxysuccinic and peroxymalonic acid. It should be noted that both the peroxy-succinic and peroxymalonic acid may come from alpha-keto dicarboxylic acids. Furthermore, because these acids exist in the Krebs cycle they are metabolically active. In some embodiments, the peroxyacid has the same number of carbons as one of the carboxylic acids.

In some embodiments, the peroxyacid is peroxyacetic acid. Peroxyacetic (or peracetic) acid is a peroxycarboxylic acid having the formula: $CH_3COOH$. Generally, peroxyacetic acid is a liquid having an acrid odor at higher concentrations and is freely soluble in water, alcohol, ether, and sulfuric acid.

In some embodiment, the peroxyacid may be a ready-to-use solution or a dilatable solution, which enables easy distribution of the composition. The peroxyacid may be any of the peroxyacids described above. In one embodiment, the peroxyacid is peroxyacetic acid.

In some embodiments, the composition may include at least one peroxyacid at an equilibrium concentration of from 1 ppm to 20 weight percent, based on the weight of the composition. In some embodiments, the peroxyacid may be present at a concentration of less than 5 weight percent, or less than 1 weight percent. In some embodiments, the amount of peroxyacid ranges from about 1.25% to about 20%, from about 2% to about 20%, from about 2% to about 10%, from about 2% to about 6%, from about 1% to about 10%, from about 1% to about 6%, from about 0.02% to about 6%, or from about 1.25 to about 3.5%, all by weight of the composition. In some embodiments, the composition may be highly diluted, having an amount of peroxyacid ranging from about 0.0001% to 3.5%, 0.0001 to 2.5% or 0.0001 to 1%, all by weight.

In addition to the peroxyacid, the composition contains a hydroperoxide. By "hydroperoxide" is meant a compound containing an $O_2H$ group. Examples of suitable hydroperoxides include, for example, hydrogen peroxide. In one embodiment, the composition contains hydrogen peroxide, in addition to at least one of methylhydroperoxide or hydroxymethyl hydroperoxide. In some embodiments, the amount of hydroperoxide ranges from about 0.1% to about 25%, from about 0.1% to about 12%, 5% to about 25%, from about 5% to about 20%, from about 7% to about 20%, from about 7% to about 14%, or from about 7% to about 12%, all by weight. When the hydroperoxide is hydrogen peroxide, hydrogen peroxide quantities disclosed herein are expressed as neat values, and are not quantities of hydrogen peroxide in solution. It should be noted that water in the aqueous composition includes water derived from the aqueous hydrogen peroxide used in the composition. Any suitable aqueous hydrogen peroxide may be used in the composition, such as for example those containing up to 30% by weight, or up to 50% by weight of hydrogen peroxide.

In some embodiments, the composition may also contain a parent carboxylic acid corresponding to the peroxy acid. As used herein, the term "parent carboxylic acid" refers to the corresponding carboxylic acid that the peroxyacid is derived from, or is degraded into under a typical storage or production conditions.

The carboxylic acid can be $C_{2-10}$ fatty acid, dicarboxylic acid, tricarboxylic acid, α-keto carboxylic acid, β-keto carboxylic, or a mixture thereof. Non-limiting examples of suitable carboxylic acids include, acetic acid, propionic acid, citric acid, succinic acid, glutaric acid, adipic acid, suberic acid, malonic acid, lactic acid, glycolic acid, oxalic acid, pyruvic acid, citramalic acid, acetoacetic acid, citraconic acid, maleic acid, and a mixture thereof.

In some embodiments, the one or more carboxylic acids, individually or totally, range from about 0.1% to about 30%, fro about 0.1% to about 12%, from about 5% to about 30%, from about 7% to about 25%, from about 7% to about 22%, from about 5% to about 20%, from about 7% to about 20%, or from about 7% to about 12% all by weight in the composition.

In one embodiment, the composition includes one or more hydroperoxides in an amount ranging from about 0.01% to about 25% by weight; one or more carboxylic acids in an amount ranging from about 0.01% to about 30% by weight; and one or more peroxyacids in an amount ranging from about 0.0001% to about 20% by weight. In one embodiment, the composition includes one or more hydroperoxides in an amount ranging from about 5% to about 25% by weight; one or more carboxylic acids in an amount ranging from about 7% to about 30% by weight; and one or more peroxyacids in an amount ranging from about 1% to about 10% by weight. In another embodiment, the composition contains hydrogen peroxide in an amount ranging from about 7% to about 12% by weight; acetic acid in an amount ranging from about 7% to about 12% by weight; and peracetic acid in an amount ranging from less than 1.25% to about 3.5% by weight.

In some embodiments, the composition may also contain one or more additional acids, such as for example, at least one of acid, citric acid, succinic acid, glutaric acid, adipic acid, suberic acid, malonic acid, lactic acid, glycolic acid, oxalic acid, pyruvic acid, tartaric acid, formic acid, cis-epoxysuccinic acid, methyltartaric acid, acetic acid, cis-epoxymethylsuccinic acid, maleic acid, citramalic acid, acetoacetic acid, citraconic acid. In some embodiments, the composition further contains at least one of citramalic acid, acetoacetic acid, citraconic acid, maleic acid and any mixture thereof.

In some embodiments, the composition of any of the embodiments may include other compounds. In some embodiments, the composition may also contain a bis(hydroperoxide). Suitable bis(hydroperoxides) include, for example, 3,3-bis(hydroperoxy)butanoic acid, 3-bis(hydroperoxy)butaneperoxoic acid, bis(hydroperoxy)propane, or combinations thereof. It was particularly unexpected that stable compositions of peroxyacids and bis(hydroperoxides) could be prepared, since peroxyacids are very strong oxidizing agents even at a pH of 2 to 8 because the water soluble peracids are decomposing to form free radicals.

In some embodiments, the composition may also contain an epoxide.

In some embodiments, the composition may also contain a salt or anhydride of the peroxyacid. Suitable salts include, for example, a lithium, sodium, potassium, rubidium, cesium, zinc, magnesium, or calcium salt, or a mixture thereof. The salt can be a magnesium salt such as magnesium hydroxide, magnesium carbonate, magnesium salt of peracetic acid, and the like. In one embodiment, the salt is a magnesium salt of peracetic acid, such as, for example, magnesium acetate tetrahydrate.

In one embodiment, the composition also includes at least one oxidized acetoacetate compound.

The composition may be prepared by any suitable method. The methods of some embodiments of the invention include contacting at least one carboxylic acid, such as acetic acid, or a salt of anhydride thereof, and at least one oxidizing agent, such as hydrogen peroxide. When describing a chemical reaction, the terms "treating," "contacting," and "reacting" are used interchangeably herein, and refer to adding two or more reagents under appropriate conditions to produce the indicated and/or the desired product. The molar ratio of oxidizing agent to carboxylic acid typically ranges from about 0.5:1 to about 2:1, often about 2:1 to about 6:1. A molar ratio above 1:1 is preferred. The method produces a reaction mixture containing at least one peroxyacid at least one carboxylic acid and at least one hydroperoxide. Exemplary oxidizing agents that are useful in methods of the invention include, but are not limited to, hydrogen peroxide, barium peroxide, sodium carbonate peroxide, calcium peroxide, sodium perborate, lithium peroxide, magnesium peroxide strontium peroxide, zinc peroxide, potassium superoxide, and the like.

The reaction is generally conducted in an aqueous solution. Other solvents, such as an organic solvent can also be used in addition to or in place of the aqueous solution. Because it is inexpensive and commercially available in an aqueous solution, typically hydrogen peroxide is used as an oxidizing agent.

In some embodiments, additional reagents may be used in the reaction, such as, for example acetic anhydride, maleic acid or anhydride, citraconic acid or anhydride, or a mixture thereof.

The methods of other embodiments of the invention involve preparing admixtures of the key composition components. In one embodiment, the admixture contains a hydroperoxide, a peroxyacid, and a parent carboxylic acid corresponding to the peroxy acid. Suitable hydroperoxides are as described hereinabove. In one embodiment, the peroxyacid is peracetic acid, the parent carboxylic acid is acetic acid, and the hydroperoxide is hydrogen peroxide. In another embodiment, the admixture contains hydrogen peroxide, a peroxyacid, such as peracetic acid, and one or more optional compounds such as tartaric acid, formic acid, cis-epoxysuccinic acid, methyltartaric acid, cis-epoxymethylsuccinic acid, maleic acid, citramalic acid or citraconic acid. In one embodiment, the admixture contains hydrogen peroxide, acetic acid and the peroxyacid thereof, peracetic acid.

The compositions of the invention are stable. The composition may be in any suitable, stable form, for example a gel, sol, liquid, lotion, irrigation gel, or spray. For the purpose of this invention, a "stable" composition is one that maintains sufficient physical properties and active oxygen content long enough to be useful, for a period of about twelve months.

In some embodiments, the composition may be useful for at least one of healing of wounds after exposure to chemical and biological warfare agents, decontamination of wounds or skin after exposure to chemical and biological warfare agents, and decontamination of surfaces that have been exposed to chemical and biological warfare agents. Chemical and biological warfare agents agents are extremely toxic synthetic chemicals that can be dispersed as a gas, liquid or aerosol or as agents adsorbed to particles to become a powder. These chemical and biological warfare agents have either lethal or incapacitating effects on humans.

Chemical warfare agents are usually classified by their effects into nerve agents, blistering agents, blood agents, choking agents, psychomimetic agents (produce changes in thought, perception and mood) and toxins. Among the thousands of toxic substances that are known, only some of them are considered chemical warfare agents based on their characteristics, including high toxicity, imperceptibility to senses and rapidity of action after dissemination and persistency. Those toxic chemicals qualifying as chemical warfare agents and are listed as scheduled chemicals in the Chemical Weapons Convention (Convention on the Prohibition of the Development, Production, Stockpiling and use of Chemical Weapons and Destruction, Technical Secretariat of the Organization for Prohibition of Chemical Weapons, The Hague, accessible through internet. 2005; http://www.opcw.org).

The compositions disclosed herein may be used for decontamination of essentially any chemical warfare agents. In some embodiments, the composition may be useful for decontaminating at least one of V-series nerve agents, G-series nerve agents, A-series nerve agents and mustard agents. Examples of V-series agents include VE, VG, VM, VR, VX and analogues thereof. Examples of G-series agents include GA (tabun), GB (sarin), GD (soman), GF (cyclosarin). Examples of mustard agents include H, HD, $HN_1$, $NH_2$, $HN_3$, HL, and HT. Examples of A-series agents include A-230, A-232, A-234, Novichok-5, Novichok-7 and Substance-33. Use of the composition for wound decontamination, or skin decontamination, after chemical agent exposure is particularly important, as the skin is a primary route of exposure to chemical agents that may be used as weapons of mass destruction. Likewise, use of the composition for decontamination of surfaces that have been exposed to chemical or biological warfare agents is important because the agents remaining on those surfaces present a risk to persons who touch the contaminated surfaces. The composition may be used to decontaminate any surface, such as for example, the surface of equipment, protective gear, or any other type of object. In one embodiment, the composition may further include a nerve gas antidote. In one embodiment, the nerve gas antidote may be included in a kit including the composition.

The composition may be used to decontaminate surfaces by contacting the composition with the surfaces, which may include, for example human skin, human wounds, or non-human surfaces. The contact may be made by any suitable methid, such as for example, soaking human skin, a human wound or a nonhuman surface in a solution of the composition, dispensing a pressurized solution of the composition onto the human skin or the nonhuman surface, or applying a coating or layer of the composition on the human skin, human wound or nonhuman surface, for example, by wiping and/or scrubbing with an absorbent sponge, woven fabric, cloth, pad, towelette, or the like, soaked with the composition.

Additional objects, advantages, and novel features of this invention will become apparent to those skilled in the art upon examination of the following examples thereof, which are not intended to be limiting. In the Examples, procedures that are constructively reduced to practice are described in the present tense, and procedures that have been carried out in the laboratory are set forth in the past tense.

For clarity, terms used herein are to be understood as described herein or as such term would be understood by one of ordinary skill in the art of the invention. Additional explanation of certain terms used herein, are provided below:

Unless otherwise indicated, all numbers expressing quantities of ingredients, dimensions, reaction conditions, and so forth, used in the specification and claims, are to be understood as being modified in all instances by the term "about".

In this application and the claims, the use of the singular includes the plural unless specifically stated otherwise. In addition, use of "or" means "and/or" unless stated otherwise. Moreover, the use of the term "including", as well as other forms, such as "includes" and "included", is not limiting. Also, terms such as "element" or "component" encompass both elements and components comprising one unit and elements and components that comprise more than one unit unless specifically stated otherwise.

"wt %" refers to the weight percent relative to the total weight of the solution or dispersion.

"Film-forming agent" or "water soluble or water dispersible coating agent," which may be used interchangeably herein, refer to agents that form a film and are employed to provide protective coating to the surface of interest. These agents are either water soluble or water dispersible. These agents are described in further detail below.

"Locus" as used herein, comprises part or all of a target surface suitable to be coated.

While the invention has been particularly shown and described with reference to a number of embodiments, it would be understood by those skilled in the art that changes in the form and details may be made to the various embodiments disclosed herein without departing from the spirit and scope of the invention and that the various embodiments disclosed herein are not intended to act as limitations on the scope of the claims. All references cited herein are incorporated in their entirety by reference.

EXAMPLES

The present invention is described more fully by way of the following non-limiting examples. Modifications of the examples will be apparent to those skilled in the art.

Example 1

This example compared the effectiveness of the composition of the invention as a decontamination (DC) product after skin exposure to the chemical warfare agent VX, as compared to that of Reactive Skin Decontamination Lotion (RSDL), which is a mixture of potassium 2,3-butanedione monoximate (KBDO) and diacetylmonoxime (DAM) in a solvent of polyethylene glycol monomethyl ether (MPEG) and water. The composition contained a concentrated solution of 10.7 wt % peracetic acid, 19.8 wt % hydrogen peroxide and 16.8 wt % acetic acid.

Experimental Methods

Animals: Male guinea pigs [Hartley, Crl(HA)BR] ranging in weight from 340-503 gm at the time of experimentation were obtained from Charles River (Canada). After arrival, the animals were maintained in quarantine for at least 5 days prior to use in an Association for Assessment and Accreditation of Laboratory Animal Care International (AAALACI) accredited animal care and use facility. On the morning of an experiment, around 0800 hr, animals were weighed, the fur was carefully removed from the left side with electric clippers, and excess loose fur was removed with a vacuum. An exposure site was outlined with an indelible marker at approximately the same location on the left side of each animal midway between the spine and the ventral midline. The animals remained unanesthetized during the entire experiment. After exposure to the VX and decontamination with the composition or RSDL, animals were housed in individual cages without bedding in a fume hood for the duration of the experiment (24 hr). Food and water were provided ad libitum after exposure and DC.

Materials: Each exposure day a 50 pl aliquot of neat VX was obtained from the Chemical Exclusion Area, United States Army Medical Research Institute of Chemical Defense (USAIVIRICD; Maryland, USA). RSDL was purchased in sealed packages from First Line Technology, (Chantilly, VA). The composition according to the invention, containing peracids, was prepared. A 1:6 dilution in deionized water was prepared according to the manufacturer's formula each test day.

VX Exposure: Neat VX was applied in a fume hood to the marked exposure site of each animal, using either a 5 pl Hamilton syringe for volumes greater than 1 pl, or a 0.5 pl or 1.0 pl Hamilton digital sutyringe for volumes less than 1 pl. Animals were hand restrained by a trained technician for exposure.

Decontamination procedure: Two minutes after applying VX to the skin, the exposure site was decontaminated with RSDL or the composition. Animals were hand restrained by a trained technician during the DC procedure. RSDL was applied with an applicator made by stapling ¼ (25 mm×50 mm) of a RSDL sponge pad to a wooden tongue depressor. Applicators for the composition were made by stapling a similar size folded gauze pad to wooden tongue depressors. A fresh applicator of each DC product was used on each animal. The RSDL applicators were made just before the start of the experiment and were placed into small plastic bags until use. The composition applicators were wetted with 10 ml of the diluted composition solution just before DC. Ten ml was sufficient to saturate the applicator pad without run-off based on previous experience using dilute bleach or soap and water. RSDL and the composition DC were performed by swiping the applicator across the exposure site 10 times from a head to tail direction. Neither DC product was removed after application.

Experimental Design: VX dose-lethality curves were generated for RSDL and the composition, based on 24 hr responses. After exposure and DC, each animal was monitored continuously until the onset of toxic signs, and then at 2 and 4 hr after DC, and again 24 hr after exposure. A modified stage-wise adaptive dose design was used to generate the VX dose-lethality curves for each DC product. The first stage utilized the classic up-down dose design of Dixon to estimate the $LD_{50}$ of VX for each DC product. Briefly, one animal at a time was challenged with a dose of VX for each DC product during Stage 1. After the 24 hr response was determined, the next animal in each DC product group received a higher (if alive at 24 hr) or lower (if dead at 24 hr) dose of VX, depending on the response of the previous animal. The up-down procedure continued until four response reversals were observed. The 24 hr responses for each DC product from Stage 1 were analyzed by probit analysis using SAS NLIN and special purpose probit programs developed by Battelle (Columbus, Ohio) to generate an interim $LD_{50}$ estimate. The next stages of the experiment used 3-8 animals per stage and various doses of VX in each stage for each DC product to improve the $LD_{50}$ estimate and generate 95% confidence intervals (CI) by both the Fieller's and the delta methods. The VX doses in each stage were selected to improve the $LD_{50}$ estimate and 95% CI based from all stages. Interim probit analyses were run after each stage, and the experiment was stopped when the ratio of the upper delta 95% CI minus the lower delta 95% CI divided by 2 times the $LD_{50}$ estimate was <0.4. A total of 15 and 26 animals were used to generate the RSDL and composition dose-lethality curves, respectively.

Statistical Analysis: A final probit analysis was conducted on all stages from the 24 hr responses for RSDL and the composition. The slopes, $LD_{50}$s as well as the $LD_1$, $LD_{10}$, $LD_{16}$, $LD_{30}$, $LD_{70}$, $LD_{84}$, $LD_{90}$, and $LD_{99}$ with their respective 95% CI were calculated by both Fieller's and delta methods. Probit estimates were calculated using both target and actual doses of VX and were not statistically different; therefore, the target doses were used for all statistical comparisons and in the graphs and tables. $LD_{50}$ estimates for RSDL and the composition were compared using SAS and another specialized probit program, which determined whether the ratio of the $LD_{50}$s was statistically different at p<0.05. A significant (p<0.05) difference was achieved when the delta 95% CI of the $LD_{50}$ ratio did not include the value of 1. The slopes of the dose-lethality curves were compared according to Zar. A protective ratio (PR) defined as $LD_{50}$ of VX in animals treated with the DC product divided by the $LD_{50}$ of VX in untreated animals was estimated, using a historic value of 140 μg/kg in fur-clipped unanesthetized guinea pigs (Clarkson, personal communication) for the denominator in the ratio. The PR expresses the magnitude of the increase in the $LD_{50}$ by the DC product. Another ratio called an absolute efficacy ratio (AER) was also calculated. The AER was defined as the $LD_{10}$ of VX in animals treated with a DC product divided by the dermal $LD_{90}$ of VX in untreated animals. A $LD_{90}$ value of 188 μg/kg generated in hair-clipped, unanesthetized guinea pigs (Clarkson, personal communication) was used for the denominator for the AER. The AER expresses the magnitude of the increase in the $LD_{10}$ relative to the untreated $LD_{90}$, and is a more operationally relevant measure of efficacy than the PR, especially if the slopes of the dose-lethality curves are significantly different. Military requirements documents prescribe 80-90% survival for acceptance of new medical countermeasures against nerve agent intoxication.

Results:

FIG. 1 graphs the probit dose-lethality curves for VX in composition and RSDL-decontaminated animals, and Table 1 summarizes the results based on $LD_{50}$s. A total of 15 and 26 animals were needed to generate the dose-lethality curves for RSDL and the composition, respectively, using the stopping criteria described in the methodology. The 24 hr dermal $LD_{50}$ of VX was 5959 µg/kg in animals decontaminated with the composition and 3380 µg/kg in animals decontaminated with RSDL. The composition was 1.8-fold ($p<0.05$) more effective than RSDL. The slope of the composition dose-lethality curve was significantly ($p<0.05$) different from the slope of the RSDL dose-lethality curve. The estimated PR (treated to untreated) was 42.6 for the Composition® and 24.1 for RSDL.

TABLE 1

Twenty-four hour $VX_{LD50}$ Estimates in Guinea Pigs Decontaminated with the Composition or RSDL 2 Min After Dermal Exposure

| DC Product | Number of Animals | Slope of the Dose-Lethality Curve | 24 hr VX $LD_{50}$, µg/kg, p.c. (95% CI) | Estimated Protective Ratio[1] |
|---|---|---|---|---|
| Composition | 26 | 6.4 | 5959 (4858-7309) | 42.6 |
| RSDL | 15 | 12.7 | 3380 (2921-3910) | 24.1 |
| Efficacy Ratio | | | Composition/RSDL = 1.8 p < 0.05 50% Survival | |

Estimated using a 24-hour dermal VX $LD_{50}$ of 140 µg/kg in fur-clipped unanesthetized guinea pigs (Clarkson, personal communication)

Table 2 summarizes the results based on $LD_{10}$s. The 24 hr dermal $LD_{10}$ of VX was 3755 µg/kg in animals decontaminated with the composition and 2681 µg/kg in animals decontaminated with RSDL. The composition was 1.4-fold more effective than RSDL; this difference was not significant. Also, presented in Table 2 is the ratio of the VX $LD_{10}$ in animals receiving DC to the VX $LD_{90}$ in animals that were not treated with a DC product. The $LD_{10}/LD_{90}$ ratio for the composition was 20 and the ratio for RSDL was 14.

TABLE 2

Twenty-Four Hour VX $LD_{10}$ Estimates in Guinea Pigs Decontaminated with the Composition or RSDL 2 Min After Dermal Exposure

| DC Product | Number of Animals | 24 hr VX $LD_{10}$, µg/kg, p.c. (95% CI) | $LD_{10}/LD_{90}$ [1] |
|---|---|---|---|
| Composition | 26 | 3755 (2390-5500) | 20 |
| RSDL | 15 | 2681 (2096-3429) | 14 |
| Efficacy Ratio | | Composition/RSDL = 1.4 90% Survival | |

VX $LD_{90}$ of 188 µg/kg was used for the denominator. This value was estimated from the dose-lethality curve generated in fur-clipped, unanesthetized guinea pigs (Clarkson, personal communication)

A comparison of the $LD_{50}$ estimates showed that the composition was significantly more effective than RSDL. In addition, the slope of the composition dose-lethality curve was more shallow than the slope of the RSDL curve. It is not unusual for the slope of the dose-lethality curve to become more shallow as the effectiveness of medical countermeasures against organophosphate intoxication increases. However, Braue et al. observed no difference in the slopes of the dose-lethality curves for RSDL, 1% soapy water, and 0.5% bleach, even though RSDL was greater than 3-fold more effective than the other two DC products; all three slopes were similar to the slope for the composition in the study.

When the slopes are different, comparison of $LD_{50}$s may not be as valuable, because the lower doses of agent in the curve with the shallower slope may still show lethality. Since the slope of the composition dose-lethality curve was shallower than the slope of the RSDL curve, the ratio of the $LD_{10}$ doses of VX were compared. This might reveal whether the shallower slope of the composition dose-lethality curve resulted in higher lethality at lower doses of VX compared to RSDL. The $LD_{10}$ was selected because military requirements documents prescribe 80-90% survival rates as criteria for accepting new medical countermeasures for use by warfighters. The composition was still more effective than RSDL, but the ratio of the $LD_{10}$s was not significantly different. This was probably due to the wider confidence intervals around the $LD_{10}$ than the $LD_{50}$ estimate. The ratio of the $LD_{10}$ in the animals receiving DC to $LD_{90}$ in animals not receiving DC provides another way of comparing efficacy which is independent of the slope. This ratio value represents the number of $LD_{90}$s of exposure that can be tolerated without sustaining more than 10% lethality. This value was 20 for the composition and 14 for RSDL.

Example 2

This example involved an In vitro evaluation of the composition of the invention by nuclear magnetic resonance (NMR) evaluation. The composition contained a concentrated solution of 10.7 wt % peracetic acid, 19.8 wt % hydrogen peroxide and 16.8 wt % acetic acid.

Summary: A decontamination (DC) solution containing the composition was examined for its ability to breakdown intact chemical warfare agents (CWAs) in vitro using nuclear magnetic resonance spectroscopy (NMR). Agents examined were HD, GD, VX, VR and A-232. For all agents except HD, the assessment was done with one-dimensional heteronuclear spin quantum correlation (HSQC) techniques. This approach has been successfully utilized for similar studies examining the breakdown kinetics in enzyme systems using comparable agent levels. For HD, direct one-dimensional proton experiments were used.

Composition Sample Preparation: Dilutions of the composition were made with 99.5% $D_2O$ from Sigma-Aldrich. Final concentrations of 2 wt %%, 4 wt % and 6 wt % of peracetic acid were achieved after mixing 100 µL of CWA with 500 µL of the composition.

Agent Preparations: CWAs were provided in deuterated solvents by the MRICD Chemical Exclusion Area where the concentrations of each of the CWAs were determined independently. For all experiments, 100 µL of CWA was mixed with 500 µL of the composition. For kinetic determinations, the peak area at time zero was set equal to the final amount of CWA after dilution with the composition. Time zero amounts were 912.8, 175.7, 95.3, 88.0 and 77.7 for HD, GD, VX, VR and A-232, respectively.

Instrumentation: NMR data on VX, VR, GD and A-232 were collected on a 3-channel Bruker Avance III Ultrashield 500 MHz NMR spectrometer (Bruker Biospin, Billerica, Mass.) equipped with a Z-gradient 5 mm BBO probe head at 25° C. Topspin (Bruker 3.2 pl6) was used for data acquisition and processing. Dynamics Center v2.2 was used for kinetic analysis, and results were exported to PDF and Excel formats, which later were analyzed using GraphPad's Prism5 for Windows.

NMR data on HD were collected on an Agilent (Agilent Systems, Santa Clara, CA) 4-channel DD2 Actively Shielded 600 MHz NMR instrument equipped with a 5 mm PFG Penta probe at 25° C. VNMRJ 3.2 was used for data collection and processing, and the results were exported to Excel for kinetic analysis.

Figure 3:
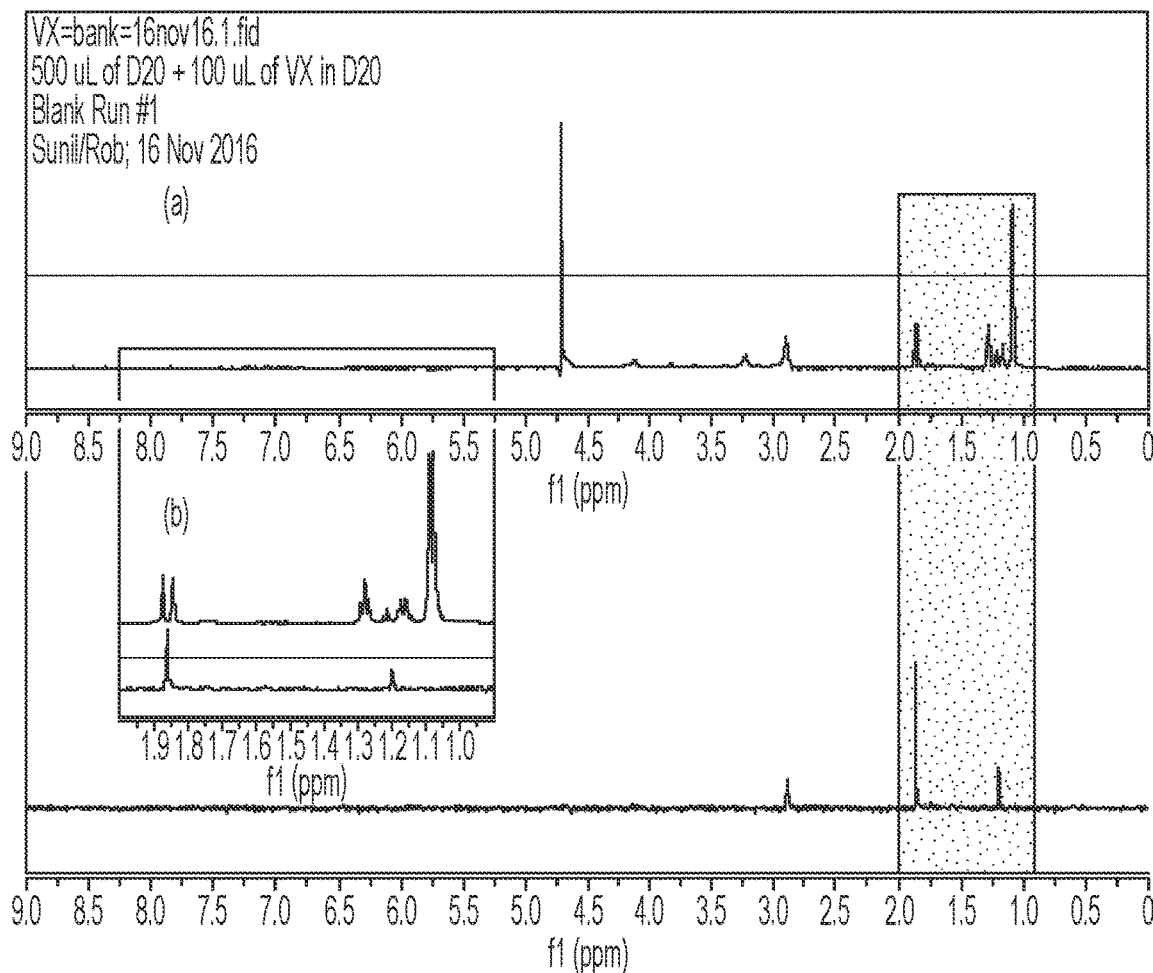
FIG. 3 is a depiction of an NMR spectrum of (a) chemical warfare agent VX and (b) its decontamination product.

Experimental Design: For all experiments 100 µL of CWA was added to 500 µL of the composition or D2O as per experimental protocol. Proton one-dimensional experiments were carried out with or without pre-saturation of water signal. The offset carrier frequency was adjusted on water resonance, and minimum power level was used to saturate the water signal without distortion/perturbation of the neighboring resonances. All samples were temperature equilibrated, and the probe was tuned to the respective frequencies followed by gradient shimming. The time required for gradient shimming (dead time) was noted and taken into account for all kinetic calculations. Ninety degree pulse width, X pwx, and decoupling calibrations were done on both the proton and phosphorus channels and saved in the probe files, respectively. Proton one-dimensional pulse sequence (s2pul) was used in HD, and modified gradient $^1$H-X 1D-HSQC (FIG. 2) was used for all other CWAs. (A representation of the gHSQC1D experiment is presented in FIGS. 3a and 3b showing expansion of the region of interest of methyl resonances —P-CH$_3$ at 1.96 and 1.20 ppm, respectively.) Optimization of the proton signal at 1.96 ppm in $^1$H-X Heteronuclear Single Quantum Coherence (HSQC) was done by observing $^nJ_{HX}$ coupling constant (Table 3) and changing the J parameter in the pulse sequence to the observed value. The ratio of G1/G2 gradient strength was also optimized to give an optimum signal, and this is based on the gyromagnetic ratio of proton and phosphorus.

TABLE 3

Coupling Constants for Various Chemical Warfare Agents

| $^nJHX$ | Coupling Constant (Hz) |
|---|---|
| $^2JHX$ VX | 17.5 |
| $^2JHX$ GD | 18.5 |
| 2J HX VR | 17.5 |

Proton spectra were acquired on all CWAs to check the purity of the compound and to determine whether any degraded products were present. Background spectra were acquired on all composition samples before 100 µL of respective agent was added to the NMR tube. All gHSQC1D spectra were acquired with the same parameters (nt/ns=16; relaxation delay (d1)=2 sec; dummy scans (ss/ds)=0; acquisition time (at)=1.7 s; number of data points (np)=32K, Fourier number (fn)=64K) and processed using Bruker Biospin and/or VNMRJ with zero filling to 64K data size and applying exponential weighting function line broadening (LB) of 1.0 Hz.

Peak integrals were manually defined based on methyl peaks from starting material and methyl peaks from intermediate compound. These methyl peaks were identified by using an edited version of (gradient heteronuclear single quantum coherence with adiabatic pulses) gHSQCAD two-dimensional experiment and the peaks' chemical shifts. Total acquisition time for all kinetic experiments was adjusted to 1 hour. Triplicate data sets were collected for each of the four CWA and blank runs. Blank runs were done in 99.8% D2O without the composition and monitored for a total of 1 hr. Kinetic data are summarized in Tables 4 and 5.

TABLE 4

Half-Lives of CWAs Decontaminated with the composition Solutions

| | Blank | 2% Composition | 4% Composition | 6% Composition | RSDL |
|---|---|---|---|---|---|
| | | T½ (min) (95% Confidence Interval) | | | |
| HD | 8.6 | 51.6 | 27.9 | 19.7 | NA |
| | (8.4-8.8) | (51.4-51.7) | (27.7-28.1) | (19.55-19.79) | |
| GD | N/A | 1036 | 797 | 915 | NA |
| | | (907-1210) | (709-910) | (680-1398) | |
| VX | N/A | 39.7 | 19.2 | 13.7 | 4.6 |
| | | (38.5-41.0) | (18.9-19.5) | (13.43-13.89) | (4.4-4.9) |
| VR | N/A | 30.0 | 14.9 | 12.5 | NA |
| | | (29.3-30.7) | (14.6-15.1) | (12.3-12.8) | |
| A-232 | N/A | 163 | 95.3 | 54.3 | NA |
| | | (135-206) | (85-108) | (50.6-58.6) | |

TABLE 5

Percentage of CWA Remaining after 60 Min Decontamination with the Composition Solution

| | Blank | 2% Composition | 4% Composition | 6% Composition |
|---|---|---|---|---|
| HD | 0 | 45 | 24 | 13 |
| GD | 97 | 93 | 90 | 95 |
| VX | 100 | 34 | 11 | 8 |
| VR | 100 | 27 | 7 | 5 |
| A-232 | 100 | 90 | 61 | 48 |

*Decomposition of HD in the blank was due to hydrolysis, while oxidative breakdown was the major route observed in the composition.

To determine the rate of hydrolysis of the CWAs in the reaction mixture, the gHSQC method was used, and the peak corresponding to the starting material was manually integrated. This integration area was then applied to all spectra to obtain the change in concentration over time. In the case of HD, one-dimensional proton spectra were used. The peak corresponding to the methylene (—CH2-) peak of the starting material was integrated manually and then was applied to all spectra collected.

Figure 4:
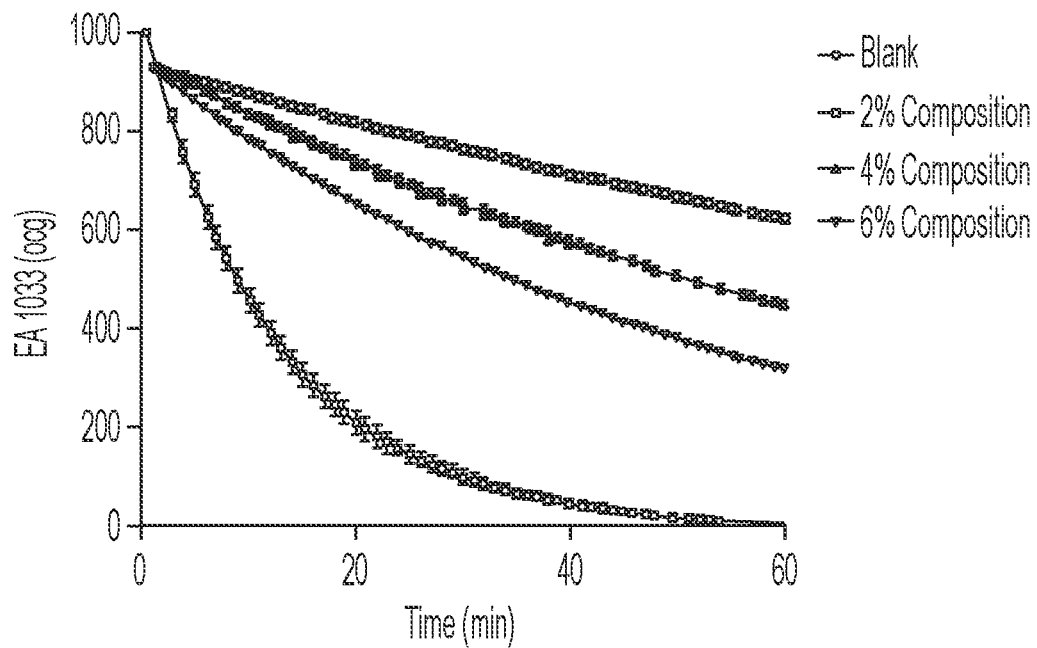
FIG. 4 is a graph showing decontamination (DC) of chemical wafare agent HD by various concentrations of a composition according to the invention fit to a one-phase decay curve.
Figure 5:
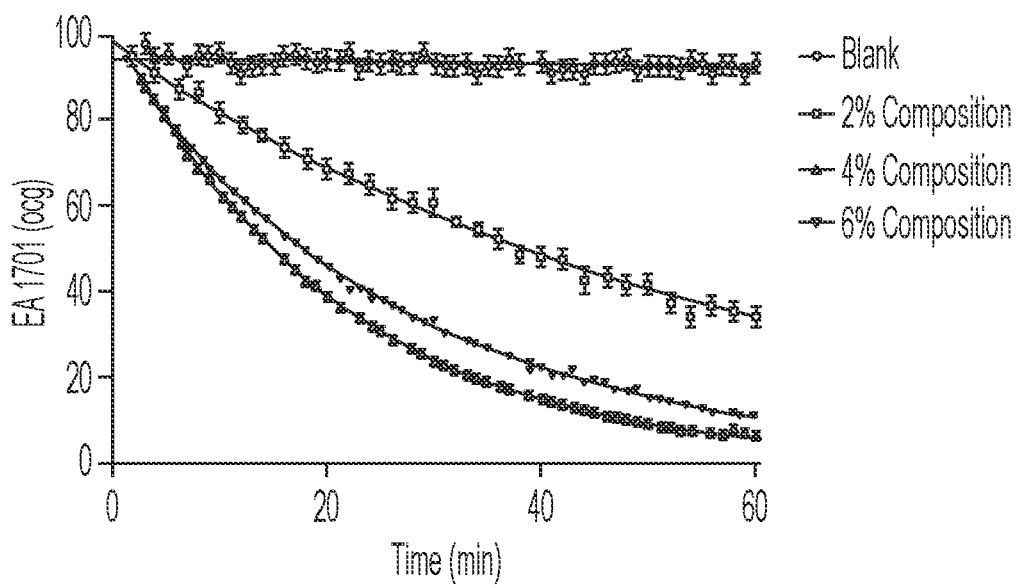
FIG. 5 is a graph showing decontamination of chemical wafare agent VX by various concentrations of a composition according to the invention fit to a one-phase decay curve.

Results: In blank composition solution (water), HD rapidly hydrolyzed with a t1/2 of 8.6 minutes (Table 4 and FIG. 4). In contrast, GD, VX, VR and A-232 were found to be stable, demonstrating that 97-100% of the starting concentration remained at the end of the experiment (Table 5). In the composition, HD breakdown was slower at all concentrations relative to the blank. Half-lives were approximately 52, 28 and 20 minutes for 2, 4 and 6%, respectively (Table 4). The differential breakdown kinetics observed between the blank and the composition solutions can be explained by the products formed. Breakdown products identified in the blank indicate hydrolysis as the primary route, whereas in the composition solutions, oxidative processes were involved. The composition demonstrated no decontamination efficacy for GD (Table 4). The amount remaining at the end of the experiment was 90% or greater at all the composition concentrations (Table 5). A concentration-dependent breakdown was observed for VX (FIG. 5) and VR in the composition. Half-lives were 39, 19 and 13 minutes for 2, 4 and 6%, respectively, for VX and 30, 15 and 12 minutes for 2, 4 and 6%, respectively, for VR (Table 4). Some breakdown of A-232 was observed in the composition compared to blank, but the rates were much less than those observed for either VX or VR in the composition (Table 4). The kinetic data are summarized in Tables 4 and 5.

Conclusion: At the time of writing, measurements by NMR of the rate at which RSDL breaks down CWAs had only been done for RSDL vs VX. It was determined that RSDL breaks down VX with a half-life of 4.6 minutes. Although the composition was slower than RSDL at breaking down VX, it was fast enough to support testing the composition in vivo.

Example 3

This example involved an initial skin DC efficacy evaluation of the composition and its comparison to RSDL following skin application of VX in guinea pigs.

Animals: The same type of animals were secured and prepared as described in Example 2.

Materials: An aliquot of neat VX was obtained from the USAMRICD Chemical Exclusion Area each exposure day. RSDL was purchased in sealed packages from First Line Technology, Chantilly, VA. The composition, containing a concentrated solution of 10.7 wt % peracetic acid, 19.8 wt % hydrogen peroxide and 16.8 wt % acetic acid, and an aliquot was diluted to a 2% peracid concentration in deionized water each test day.

Agent exposure: A vial of neat VX was obtained from the USAMRICD Chemical Exclusion Area each exposure day and placed in a fume hood at room temperature. VX was applied with a Hamilton 0.5 ul, 1 ul or 5 ul syringe equipped with a blunt tip needle and digital dispenser to the outlined exposure area.

DC Procedures: Decontamination procedures were conducted in the same manner described in Example 2.

Experimental Design: Experimental data were generated as described in Example 2.

Statistical Analysis: A final probit analysis was conducted on all stages from the 24 hr responses for each DC material. The slopes and LD50s as well as the LD1, LD10, LD16, LD30, LD70, LD84, LD90, and LD99 were calculated with their respective Fieller's and Delta 95% confidence intervals (CI). LD50 estimates for RSDL and the composition were compared using another specialized SAS program (Battelle, Columbus, Ohio), which determined whether the ratio of the LD50s was statistically different at p<0.05. A significant (p<0.05) difference was achieved when the delta 95% CI of the LD50 ratio did not include the value of 1.[5] A protective ratio (PR) defined as the LD50 of VX in animals treated with the DC product divided by the LD50 of VX in untreated animals was estimated, using a historic value of 140 µg/kg[8] in fur-clipped un-anesthetized guinea pigs for the denominator in the ratio.

Figure 6:
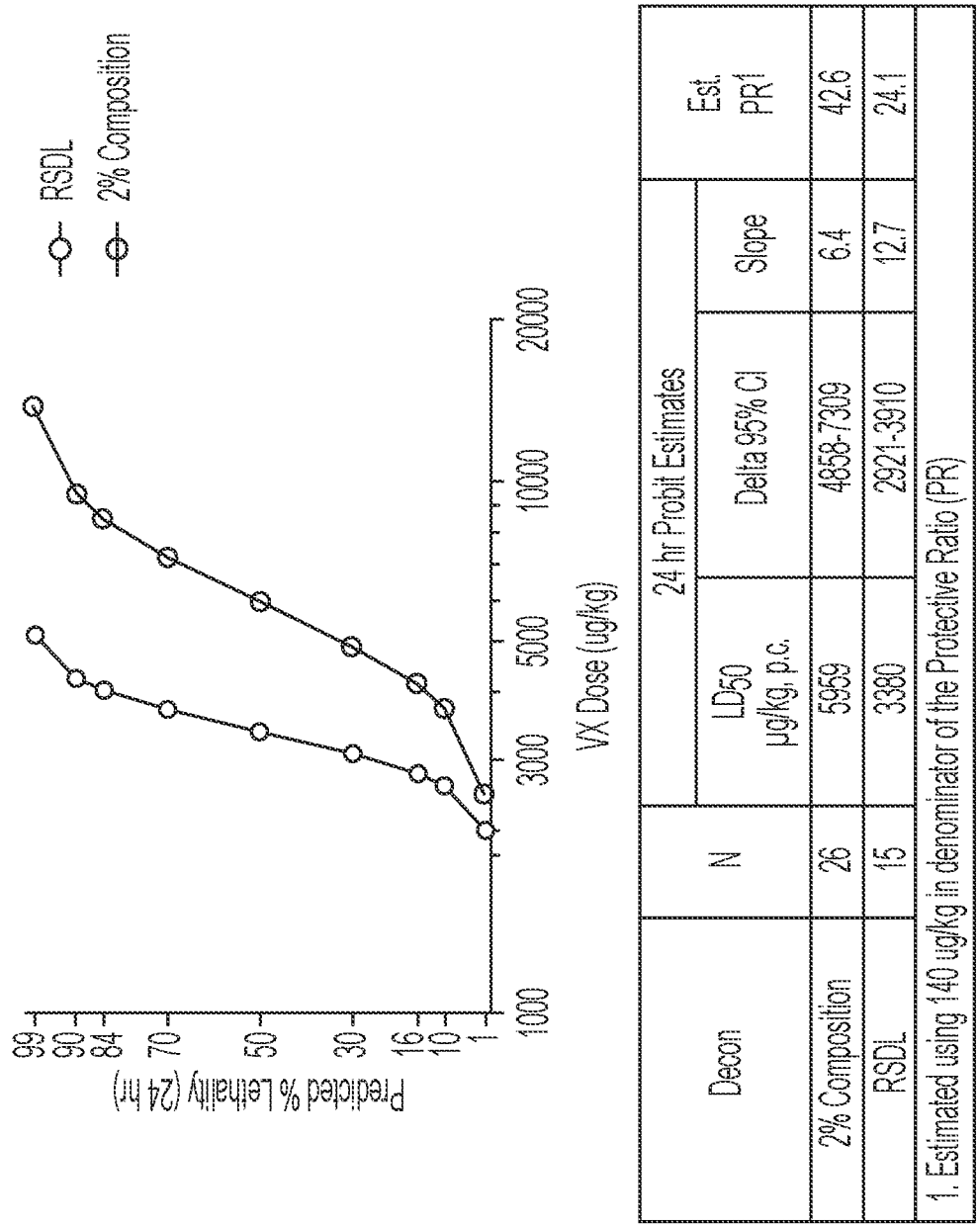
FIG. 6 a depiction of RSDL and a composition according to the invention (2%) skin decontamination (DC) efficacy following topical application of agent VX. Decontamination was performed 2 min after agent application. The graph shows the probit-predicted dose-lethality curves based on 24 hr mortality. The table shows calculated probit estimates, group sizes, and estimated protective ratios (PR).

Results: FIG. 6 graphs the probit predicted dose-lethality curves for VX in the composition- and RSDL-decontaminated animals and tabulates the probit estimates at 24 hr for the $LD_{50}$, 95% CI and slope. A total of 15 and 26 animals were needed to generate the dose lethality curves for RSDL and the composition, respectively, using the stopping criteria described above. The 24 hr dermal $LD_{50}$ of VX was 5959 µg/kg in the composition-decontaminated animals and 3380 µg/kg in RSDL-decontaminated animals. The composition was 1.8-fold (p<0.05) more effective than RSDL. The estimated PR (treated/untreated) was 42.6 for the composition and 24.1 for RSDL. Since the gauze used with the composition was more abrasive than the sponge used with RSDL, the possibility that the higher level of protection provided by the composition may have been due to increased physical removal.

Conclusion: The results of this initial assessment of the efficacy of the composition suggest that it is more effective than RSDL as a skin DC product for the nerve agent VX. However, the RSDL PR in this study is considerably lower than PRs reported by either Braue et al. or Clarkson et al.8 These investigators reported RSDL PRs of 66 (N=37) and 52 (N=53), respectively, using the same DC timing and procedures. We have no explanation for the difference in their results from ours except for the smaller sample size used in the current experiment and the inherent variability in responses of animals.

Example 4

This example analyzed delayed skin DC efficacy of the composition and RSDL following topical A-232 application in guinea pigs.

Animals: Animal information is the same as in previous studies.

Materials: An aliquot of neat A-232 was obtained from the USAMRICD Chemical Exclusion Area each exposure day. RSDL, purchased in sealed packages from First Line Technology, Chantilly, VA. The containing a concentrated solution of 10.7 wt % peracetic acid, 19.8 wt % hydrogen peroxide and 16.8 wt % acetic acid was prepared. Aliquots were diluted to a 2% peracid concentration in deionized water according to the manufacturer's formula each test day.

Agent Exposure: Exposure methods for A-232 were the same as those described for VX in previous studies.

DC Procedure: RSDL and composition applicators and DC procedures were the same as described in previous studies. Water was applied with gauze applicators saturated with 10 ml using the same procedures utilized for RSDL and the composition. A fresh applicator of each DC product was used on each animal.

Experimental Design: This study consisted of two experiments, each with 30 animals. Animals in each experiment were randomly allocated into three DC treatment groups of 10; the groups were RSDL, 2% composition, and water. In Experiment 1, animals were exposed topically to $5 \times LD_{50}$s of neat A-232, and skin DC was performed at 3 hr after agent application or at the onset of signs, whichever occurred first. In Experiment 2, animals were exposed topically to $10 \times LD_{50}$ of neat A-232, and skin DC was performed at 1 hr after agent application or at the onset of signs, whichever occurred first. The clinical condition of each animal was evaluated at 2 hr and 4 hr after DC, early the next morning (0700-0800) and at 24 hr after exposure. Clinical assessment scores (CAS) were given to the animals at each observation time according to the following scale: 0=normal appearance and behavior; 1=mildly intoxicated (characterized by slight lethargy and/or minor signs, but animal is upright and ambulates by itself); 2=moderately intoxicated (noticeable lethargy and signs, but animal is upright and will ambulate if prodded); 3=severely intoxicated (the animal is prone, not ambulatory, with prominent signs but is conscious and can lift head); and 4=very severely intoxicated (animal is prostrate, unresponsive with or without pronounced signs).

Results: Experiment 1: Six of the 30 animals developed signs of nerve agent intoxication prior to the three-hour DC time. All but one of these six animals were decontaminated at the onset of signs with their assigned DC product, and all subsequently died prior to 24 hr. The one animal that was not decontaminated developed signs within 10 min after exposure and was dead by 13 min after exposure. The remaining 23 animals reached the 3 hr DC time without exhibiting any visible signs of nerve agent intoxication. Each was decontaminated, and the survival results are summarized in Table 6. The survival rates for the RSDL, composition (2%), and water DC groups were 9/9 (100%), 7/8 (88%) and 4/6 (67%), respectively. One animal in the composition DC group was removed from the study due to a technical error.

TABLE 6

Summary of Survival from Experiment 1

| DC Product | Survival Rate | | | |
|---|---|---|---|---|
| | 2 hr | 4 hr | Next AM | 24 hr |
| RSDL | 9/9 | 9/9 | 9/9 | 9/9 |
| Composition (2%) | 8/8 | 8/8 | 7/8 | 7/8 |
| Water | 6/6 | 6/6 | 5/6 | 5/6 |

Table 7 shows the clinical assessment scores at 2 and 4 hr after DC, the next morning, and at 24 hr after exposure in the subset of 23 animals that were sign-free when DC was performed 3 hr after dermal exposure. Only one animal exhibited signs at 2 hr; this was an RSDL animal. The remaining animals that developed signs did so between 4 hr after DC and the next morning, at which time one composition animal was found dead, and two of the animals in the water group were severely affected. At 24 hr, 4/9 RSDL-decontaminated animals were normal and the remaining animals were scored as mild to moderately affected; 4/7 surviving composition animals were normal looking, and the remaining animals were mild to moderately affected. In the water DC group at 24 hr, 1/4 surviving animals appeared normal, two animals died, and three were mild to moderately affected.

TABLE 7

Clinical Assessment Scores in Individual Animals at 2 and 4 Hr after DC, the Next Morning and at 24 Hr after Exposure to 5 × LD$_{50}$ A-232 (Experiment 1)

| DC Product | Animal # | Clinical Assessment Scores | | | |
|---|---|---|---|---|---|
| | | 2 hr | 4 hr | Next AM | 24 hr |
| RSDL | 288 | 0 | N/A | 1 | 2 |
| | 291 | 0 | N/A | 0 | 1 |
| | 294 | 0 | N/A | 0 | 1 |
| | 297 | 0 | 0 | 0 | 0 |
| | 299 | 0 | 0 | 0 | 0 |
| | 301 | 0 | 0 | 0 | 1 |
| | 308 | 0 | 0 | 0 | 0 |
| | 311 | 2 | 2 | 1 | 2 |
| | 313 | 0 | 0 | 0 | 0 |
| Composition (2%) | 287 | 0 | N/A | 0 | 1 |
| | 292 | 0 | N/A | Dead | Dead |
| | 293 | 0 | N/A | 1 | 2 |

TABLE 7-continued

Clinical Assessment Scores in Individual Animals at 2 and 4 Hr after DC, the Next Morning and at 24 Hr after Exposure to 5 × LD$_{50}$ A-232 (Experiment 1)

| DC Product | Animal # | Clinical Assessment Scores | | | |
|---|---|---|---|---|---|
| | | 2 hr | 4 hr | Next AM | 24 hr |
| | 296 | 0 | N/A | 0 | 0 |
| | 305 | 0 | 0 | 1 | 1 |
| | 309 | 0 | 0 | 0 | 0 |
| | 314 | 0 | 0 | 0 | 0 |
| | 315 | 0 | 0 | 0 | 0 |
| Water | 289 | 0 | N/A | 1 | 0 |
| | 290 | 0 | N/A | 1 | 2 |
| | 304 | 0 | 0 | 3 | Dead |
| | 307 | 0 | 1 | 3 | Dead |
| | 310 | 0 | 0 | 1 | 1 |
| | 312 | 0 | 1 | 1 | 2 |

Experiment 2: Three of the 30 animals developed signs prior to 1 hr. All 3 were decontaminated with their assigned DC product at the onset of signs, and all died within 5 min after DC. The remaining 27 animals reached the one-hour DC time without exhibiting any signs of intoxication. Each was decontaminated, and the survival results are summarized in Table 8. The 24 hr survival rates were 9/9 (100%), 9/10 (90%) and 6/8 (75%) in the RSDL, the composition and water DC groups, respectively.

TABLE 8

Summary of Survival from Experiment 2

| DC Product | Survival Rate | | | |
|---|---|---|---|---|
| | 2 hr | 4 hr | Next AM | 24 hr |
| RSDL | 9/9 | 9/9 | 9/9 | 9/9 |
| Composition (2%) | 10/10 | 10/10 | 9/10 | 9/10 |
| Water | 8/8 | 8/8 | 6/8 | 6/8 |

Table 9 shows the clinical assessment scores at 2 and 4 hr after DC, the next morning, and at 24 hr after exposure in the subset of animals that were sign-free when DC was performed 1 hr after exposure. Over the course of the post-DC period, 5 of 9 RSDL animals, 6 of 10 composition animals and 6 of 8 water animals displayed signs of nerve agent poisoning of varying severity and time to onset. At 24 hr, none of the RSDL animals had died, one was very severely intoxicated, and 8 of 9 were normal looking. In the composition group, one animal died, two other animals had mild or moderate signs and 7 of 10 were normal looking. The water-decontaminated animals at 24 hr were clearly sicker than the animals in the composition and RSDL groups. Only 2 of 8 animals were normal looking, two had died, two were severely or very severely affected and two had mild to moderate signs.

TABLE 9

Clinical Assessment Scores in Individual Animals at 2 and 4 Hr after DC, the Next Morning and at 24 Hr after Exposure to 10 × LD$_{50}$ (Experiment 2)

| DC Product | Animal # | Clinical Assessment Scores (CAS) | | | |
|---|---|---|---|---|---|
| | | 2 hr | 4 hr | Next AM | 24 hr |
| RSDL | 318 | 1 | 0 | 0 | 0 |
| | 321 | 0 | 0 | 0 | 0 |

TABLE 9-continued

Clinical Assessment Scores in Individual Animals at 2 and 4 Hr after DC, the Next Morning and at 24 Hr after Exposure to 10 × LD$_{50}$ (Experiment 2)

| DC Product | Animal # | Clinical Assessment Scores (CAS) | | | |
|---|---|---|---|---|---|
| | | 2 hr | 4 hr | Next AM | 24 hr |
| | 323 | 1 | 0 | 1 | 0 |
| | 327 | 0 | 0 | 0 | 0 |
| | 330 | 0 | 0 | 0 | 0 |
| | 333* | 1 | 0 | 0 | 0 |
| | 336* | 3 | 3 | 4 | 4 |
| | 340* | 0 | 0 | 0 | 0 |
| | 344* | 2 | 2 | 0 | 0 |
| Composition (2%) | 319 | 0 | 0 | 0 | 0 |
| | 324 | 0 | 1 | 1 | 1 |
| | 325 | 0 | 0 | 2 | 2 |
| | 328 | 0 | 0 | 0 | 0 |
| | 331 | 0 | 0 | Dead | Dead |
| | 332* | 0 | 0 | 0 | 0 |
| | 334* | 2 | 0 | 0 | 0 |
| | 335* | 1 | 0 | 0 | 0 |
| | 343* | 0 | 0 | 0 | 0 |
| | 345* | 1 | 0 | 0 | 0 |
| Water | 317 | 0 | 0 | 0 | 0 |
| | 320 | 1 | 1 | Dead | Dead |
| | 322 | 0 | 0 | 2 | 3 |
| | 326 | 0 | 1 | 2 | 1 |
| | 329 | 0 | 0 | 3 | 4 |
| | 337* | 1 | 2 | Dead | Dead |
| | 339* | 0 | 0 | 0 | 0 |
| | 346* | 1 | 2 | 2 | 2 |

Conclusion: RSDL and the composition were both effective in preventing lethality when used 3 hr after dermal application of 5×LD$_{50}$ of this agent in un-anesthetized, fur-clipped animals. Each group had high survival rates at 24 hr. Mild to moderate toxic signs were present in 5/9 RSDL animals and in 4/8 of the composition animals.

The water DC group was included in the study as a control to evaluate the role of physical removal. Survival rate (83%) at 24 hr in the water group was not different from the RSDL and composition animals; however, more of the water-decontaminated animals died, showed signs of intoxication, and were more severely affected the day after exposure.

Example 5

This example analyzed skin decontamination efficacy of the composition and RSDL in guinea pigs following topical VX application, using methods that mimic mass casualty DC procedures Animals: Animal information is the same as in previous studies.

Materials: An aliquot of neat VX was obtained from the USAMRICD Chemical Exclusion Area each exposure day. RSDL sponge pads were purchased in sealed packages from First Line Technology, Chantilly, VA. Bulk RSDL was purchased from Emergent Biosolutions, Rockville, MD. The composition was prepared as a concentrated solution of 9.5 wt % peracetic acid, 17.4% hydrogen peroxide and 17.8 wt % acetic acid, and aliquots were diluted to a 2% peracid concentration in deionized water each test day.

Agent Exposure: Agent exposure method was the same as in previous VX studies.

Decontamination (DC) Procedure: The exposure site on each animal was decontaminated two minutes after VX application with tap water, 1% Dawn™ dish detergent, RSDL, or 2% composition. A three-step DC procedure designed to mimic procedures employed in a mass casualty chemical agent incident was utilized. In step 1, the DC material was applied by swiping an applicator containing the DC material 10 times quickly in short strokes across the exposure site in a head-to-tail direction; the DC material remained on the skin for 2 min. In step 2, the DC material was removed by wiping the exposure site 5 times quickly in short strokes in a head-to-tail direction with an applicator wetted with 10 ml of water. In step 3 the exposure area was dried with 5 swipes with a dry gauze applicator. Fresh applicators were used for each procedure on each animal. Water, Dawn™, and the composition were applied with fresh gauze applicators for each animal saturated with 10 ml of DC solution, as described in previous experiments. RSDL was applied using either the gauze applicator (RSDL-G) saturated with 10 ml of RSDL or the commercial sponge pad applicator (RSDL-S), as described in previous studies.

Experimental Design: VX dose-lethality curves (DLCs) were generated for all DC materials using a modified stage-wise adaptive dose design.1 Each stage consisted of a number of agent doses and animals per dose to establish the range of lethality from 0-100% and to define the response relationship in the projected middle (30-70%) of the DLC. A specialized probit analysis program (Battelle, Columbus, Ohio) and SAS NLIN were used on the cumulative results (survival/lethality) after each stage to estimate the LD$_{50}$ and 95% confidence intervals (CI) and to assess stopping criteria to limit animal use. The stage process continued with additional challenge doses and animals per agent dose until the ratio of the upper 95% CI minus the lower 95% CI (delta or Fieller's limits) divided by two times the MLD estimate from the latest stage was less than 0.4 (stopping criteria) or up to 40 animals were used. After exposure and DC, each animal was monitored continuously for up to 2 hr until the onset of toxic signs appeared, then at 4 hr after DC and again at 24 hr after exposure.

Statistics: A final probit analysis was conducted on all stages from the 24 hr responses for each DC material. The LD50s, LD1, LD10, LD16, LD30, LD70, LD84, LD90, and LD99 with their respective 95% CI were calculated by both Fieller's and delta methods, and the slopes were determined.3,4 A protective ratio (PR), defined as LD50 of VX in animals treated with each DC material divided by the historic LD50 of VX in untreated animals of 140 μg/kg8 in fur-clipped un-anesthetized guinea pigs, was calculated. This estimate was used to compare the effectiveness of the DC treatments using a specialized probit program (Battelle, Columbus, Ohio) and SAS.

Figure 7:
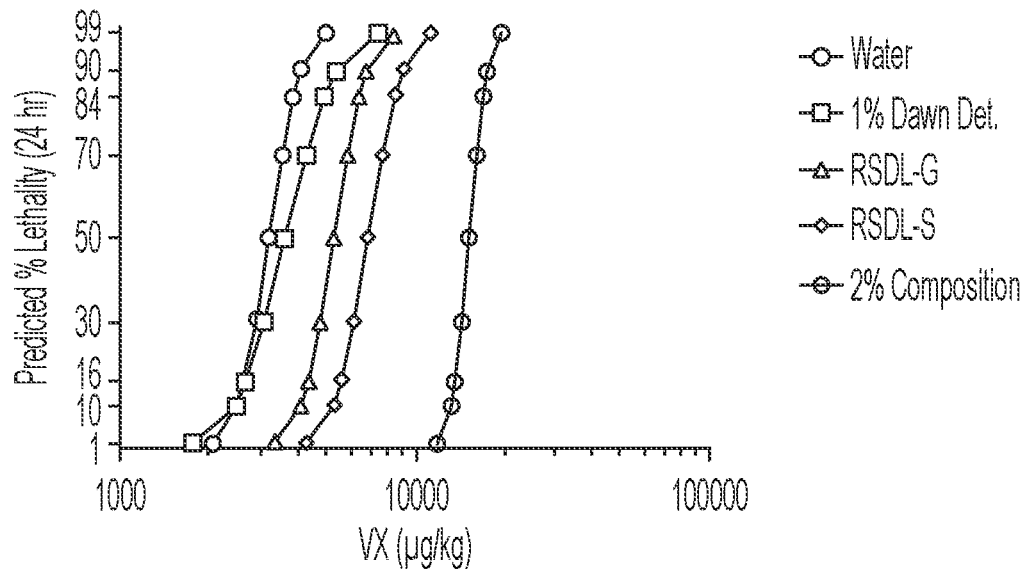
FIG. 7 is a depiction of skin decontamination efficacy of various materials using a 3-step decontamination method mimicking mass casualty procedures, following topical application of VX. The DC was performed 2 min after agent application. The graph shows the probit-predicted dose-lethality curves from 24 hr mortality. The table shows calculated probit estimates for $LD_{50}$, 95% CI, slope, group sizes, and estimated protective ratios (PR).

Results: FIG. 7 graphs the 24 hr probit-predicted VX dose-lethality curves for skin decontamination at 2 min after agent application with water, 1% Dawn™, RSDL-G, RSDL-S and 2% composition using a 3-step DC procedure as well as the probit estimates at 24 hr for the LD$_{50}$, 95% CI and slope for each DC material. The composition was significantly more effective than any of the other DC materials, with an estimated PR of 108. The composition was more than 4 times more effective than tap water or soapy water, and more than 2 times more effective than RSDL applied with the commercial sponge pad (RSDL-S) or with the gauze (RSDL-G) applicator. There was a trend suggesting that the RSDL-S was more effective than RSDL-G.

Conclusion: The composition was at least 2-fold more effective than RSDL and 4- to 4.5-fold more effective than tap water or soapy water using a 3-step skin DC methodology that mimics mass DC procedures against topically applied VX in guinea pigs. Since the composition was applied and left on the skin for only 2 min prior to rinsing and drying of the skin, the results suggest that the composition neutralized VX on skin.

Example 6

This example analyzed Skin DC efficacy of the composition and RSDL following topical VX application in swine.

Animals: Göttingen mini-pigs were acclimated to being in a transfer sling and in a cage in a fume hood. Animals were trained to respond to Gatorade, which was used to entice the animal to approach the edge of the cage with its head down so that agent could be applied to the scalp and decontamination solution could be rubbed across the exposure site. On the day of exposure, the animals were weighed, the hair on the scalp was clipped and a 1-inch diameter circle was drawn on the scalp.

Experimental Design: While the animal was being given Gatorade, $2 \times LD_{50}$ (490 µg/kg) of VX was applied using a Hamilton digital syringe to the center of the circle. At either 5 min or 1 hour after VX application, the site was decontaminated with either RSDL or the composition, by wiping the site 3 times with the DC product. Care was taken to ensure that the DC product did not enter the eye by using a piece of dry gauze. The DC product was allowed to stay on the skin for 15 minutes, then removed by wiping the site 3 times with saline-soaked gauze. Animals were observed and kept in the hood for 24 hours, with access to food and water. All surviving animals were euthanized at 24 hours. The exposure area of the scalp was removed and placed in bleach for decontamination.

Conclusion: In this mini-pig model, RSDL and the composition were comparable in decontamination effectiveness.

Many modifications and other examples of the disclosure set forth herein will come to mind to those skilled in the art to which this disclosure pertains, having the benefit of the teachings presented in the foregoing descriptions and the associated drawings. Therefore, it is to be understood that the disclosure is not to be limited to the specific examples disclosed and that modifications and other embodiments are intended to be included within the scope of the appended claims.

Moreover, although the foregoing descriptions and the associated embodiments describe aspects of the disclosure in the context of certain example combinations of structural elements and/or functions, it should be appreciated that different combinations of elements and/or functions may be provided by alternative embodiments without departing from the scope of the appended claims. In this regard, for example, different combinations of elements and/or functions than those explicitly described above are also contemplated as may be set forth in some of the appended claims. Although specific terms are employed herein, they are used in a generic and descriptive sense only and not for purposes of limitation.

What is claimed is:

1. A method of decontaminating an animal wound exposed to a chemical warfare agent, comprising contacting the wound with a decontaminating composition in an amount sufficient to decontaminate the wound, wherein the decontamination composition comprises active decontaminating compounds, and wherein the active decontaminating compounds consist of:
    peracetic acid in an amount ranging from about 2% to about 6% by weight;
    hydrogen peroxide in an amount ranging from about 3.2% to about 20% by weight; and
    acetic acid in an amount ranging from about 2.8% to about 20% by weight.

2. The method of claim 1, wherein the animal is exposed to a chemical warfare agent selected from the group consisting of a V-series nerve agent, G-series nerve agent, A-series nerve agent, mustard agent, and any combination thereof.

3. The method of claim 1, wherein the composition is formulated in a form selected from the group consisting of a gel, sol, liquid, lotion, irrigation gel, and spray.

4. The method of claim 1, wherein the decontamination composition is contacted with the wound by at least one of:
    soaking the wound in a solution of the composition,
    dispensing a pressurized solution of the composition onto the wound, or
    applying a coating or layer of the composition on wound.

5. The method of claim 1, wherein the animal is a human.

6. The method of claim 1, wherein the decontaminating composition further comprises a stabilizer selected from the group consisting of etidronic acid, disodium ethyelendiamine tetraacetic acid, ethylenediaminetetraacetic acid, tetrasodium ethylene diamine tetraacetate, citramalic acid, dipicolinic acid, dipicolinic acid N-oxide, and a combination thereof.

7. The method of claim 1, wherein the active decontaminating compounds consist of:
    peracetic acid in an amount ranging from about 2% to about 6% by weight;
    hydrogen peroxide in an amount ranging from about 5% to about 20% by weight; and
    acetic acid in an amount ranging from about 5% to about 20% by weight.

8. The method of claim 1, wherein the decontaminating composition is contacted with the wound by:
    applying the composition to the wound for a period of time, followed by wiping the site of application to remove the composition.

9. The method of claim 8, wherein the period of time is 15 minutes.

* * * * *

UNITED STATES PATENT AND TRADEMARK OFFICE
CERTIFICATE OF CORRECTION

PATENT NO. : 11,969,399 B2
APPLICATION NO. : 18/108940
DATED : April 30, 2024
INVENTOR(S) : Scott Noblitt et al.

It is certified that error appears in the above-identified patent and that said Letters Patent is hereby corrected as shown below:

On the Title Page

Item (60) Division of application No. 17/326,507, filed on May 21, 2021, which is a continuation-in-part of application No. PCT/US2021/012540, filed on Jan. 7, 2021, which is a continuation of application No. 16/900,816, filed on Jun. 12, 2020, said application No. PCT/US2021/012540 is a continuation of application No. 16/736,546, filed on Jan. 7, 2020, now abandoned, said application No. 16/900,816 is a continuation-in-part of application No. 16/736,546, filed on Jan. 7, 2020, now abandoned, which is a continuation-in-part of application No. PCT/US2018/41163, filed on Jul. 7, 2018.

Should read:
(60) Provisional application No. 63/004,858, filed on Apr. 3, 2020, provisional application No. 62/861,810, filed on Jun. 14, 2019, provisional application No. 62/530,045, filed on Jul. 7, 2017.

Signed and Sealed this
Fourth Day of June, 2024

Katherine Kelly Vidal
*Director of the United States Patent and Trademark Office*